(12) United States Patent
Doillon et al.

(10) Patent No.: US 7,476,398 B1
(45) Date of Patent: Jan. 13, 2009

(54) CORNEAL IMPLANT AND USES THEREOF

(75) Inventors: Charles J. Doillon, Quebec (CA); May Griffith, Carp (CA); Fengfu Li, Ottawa (CA); Shigeto Shimmura, Kawasaki (JP)

(73) Assignee: Universite Laval, Quebec, Quebec (CA)

( * ) Notice: Subject to any disclaimer, the term of this patent is extended or adjusted under 35 U.S.C. 154(b) by 0 days.

(21) Appl. No.: 10/606,796

(22) Filed: Jun. 27, 2003

Related U.S. Application Data

(60) Provisional application No. 60/391,942, filed on Jun. 28, 2002.

(51) Int. Cl.
*A61F 2/00* (2006.01)
*A61F 2/14* (2006.01)

(52) U.S. Cl. .................. 424/423; 424/427; 623/5.11
(58) Field of Classification Search ................ None
See application file for complete search history.

(56) References Cited

U.S. PATENT DOCUMENTS

| | | | |
|---|---|---|---|
| 4,581,030 A | 4/1986 | Bruns et al. | |
| 4,702,244 A | 10/1987 | Mazzocco | |
| 4,780,409 A | 10/1988 | Monji et al. | |
| 5,112,350 A | 5/1992 | Civerchia et al. | |
| 5,114,627 A | 5/1992 | Civerchia | |
| 5,201,764 A | 4/1993 | Kelman et al. | |
| 5,300,116 A | 4/1994 | Chirila et al. | |
| 5,401,508 A * | 3/1995 | Manesis .................... | 424/427 |
| 5,433,745 A | 7/1995 | Graham et al. | |
| 5,436,135 A | 7/1995 | Tayot et al. | |
| 5,458,819 A | 10/1995 | Chirila et al. | |
| 5,661,194 A | 8/1997 | Ando et al. | |
| 5,843,185 A | 12/1998 | Rolden et al. | |
| 5,994,133 A | 11/1999 | Meijs et al. | |
| 6,005,160 A | 12/1999 | Hsiue et al. | |
| 6,030,634 A | 2/2000 | Wu et al. | |
| 6,102,946 A | 8/2000 | Nigam | |
| 6,238,688 B1 | 5/2001 | Wu et al. | |
| 6,410,044 B1 * | 6/2002 | Chudzik et al. ............ | 424/423 |
| 6,897,064 B2 * | 5/2005 | Yoshioka et al. .......... | 435/397 |
| 2001/0018612 A1 | 8/2001 | Carson et al. | |

FOREIGN PATENT DOCUMENTS

| | | | |
|---|---|---|---|
| EP | 0387975 A1 * | 3/1990 | |
| WO | WO 9417851 A1 * | 8/1994 | |
| WO | WO 99/37752 | 7/1999 | |

OTHER PUBLICATIONS

S. Shimmura et al. Biocompatibility of Collagen-Based Blended Biomaterials, Invest Ophthalmol Vis Sci 2002;43: E-Abstract 2997, pp. 1-2.

(Continued)

*Primary Examiner*—Dave Willse
*Assistant Examiner*—Javier G Blanco

(57) ABSTRACT

A membrane for corneal implant or keratoprosthesis comprising a biological polymer and a polyacrylamide is described. The mixture of both polymers produces a hydrogel that becomes a transparent film or membrane upon drying. The resulting device and tissue engineered implants are useful for biomedical applications of the cornea, such as tissue repair and transplantation.

22 Claims, 4 Drawing Sheets

OTHER PUBLICATIONS

May Griffith et al., Functional Human Corneal Equivalents Constructed from Cell Lines, Dec. 10, 1999, vol. 286: pp. 2196-2172.

Jean-Marc Legeais et al., Nineteen Years of Penetrating Keratoplasty in the Hotel-Dieu Hospital in Paris, 2001 Cornea 20: pp. 603-606.

Jean-Marc Legeais et al., A second generation of artificial cornea (Biokpro II), Biomaterials 19 (1998) pp. 1517-1522.

Yoichi Minami et al., Reconstruction of Cornea in Three-Dimensional Collagen Gel Matrix Culture Invest. Ophthal. & Visual Science, Jun. 1993, vol. 34, No. 7, pp. 2316-2324.

Teruo Miyata et al., Collagen Engineering for Biomaterial Use; Clin. Mat. 9 (1992): pp. 139-148.

Toshiaki Takezawa et al., Cell Culture on a Thermo-Responsive Polymer Surface, Bio./Tech. vol. 8, Sep. 1990, pp. 854-856.

Toshiaki Takezawa et al., Morphological and immuno-cytochemical characterization of a hetero-spheroid composed of fibroblasts and hepatocytes, Journ. of Cell Science 101, 1992, pp. 495-501.

Vickery Trinkaus-Randal et al., Implantation of a Synthetic Cornea, Artificial Organs 21(11): 1185-1191.

V. Trinkaus-Randal et al., Biological response to a synthetic cornea, Journ. of Controlled Release 53 (1998), pp. 205, 214.

S. Vijayasekaran et al., Cell viability and inflammatory response in hydrogel sponges implanted in the rabbit cornea, Biomaterials 19 (1998): pp. 2255-2267.

Xin Yi Wu et al., In vivo comparison of three different porous materials intended for use in keratoprosthesis; Br. J. Ophthalmol 1998; 82: 569-576.

Traian V. Chirila, An overview of the development of artificial corneas with porous skirts and the use of PHEMA for such an application, Biomaterials 22 (2001) pp. 3311-3317.

P. Giusti et al., Collagen-based new bioartificial polymeric materials, Biomaterials 1994, vol. 15, No. 15: pp. 1229-1233.

Kaarina Tervo et al., Recovery of Cornea Innervation Following Photoreafractive Keratoablation, Arch Ophthalmol/vol. 112, 1994: pp. 1466-1469.

\* cited by examiner

CORNEAL IMPLANT AND USES THEREOF

CROSS-REFERENCE TO RELATED APPLICATIONS

This application claims the benefit of U.S. provisional Patent Application Ser. No. 60/391,942 filed Jun. 28, 2002, which is incorporated by reference herein in its entirety.

FIELD OF THE INVENTION

The invention relates to a corneal implant its use for a number of biomedical applications of the cornea, including keratoprosthesis, repair and transplantation. The invention further relates to a method of preparing such a corneal implant.

BACKGROUND OF THE INVENTION

The cornea protects the intraocular contents and serves as major optical element of the eye. 75% of the diopteric power of the eye depends on the interface of the cornea and air. Injury, disease or cellular failure can cause opacification of the cornea with subsequent impairment and corneal blindness. Affecting more than 10 million patients worldwide, corneal opacification is often managed by transplantation of human donor tissues. This procedure has a poor success rate in disorders such as autoimmune conditions or chemical injuries. In industrialized countries, the ageing of the population exacerbates this demand, which is compounded by the shelf-life of donated eyes being only a few days. Furthermore, in developing countries where the number of cases of cornea blindness is increasingly problematic, healthy donor tissue is rare. Alternatively, corneal transplants are needed in several third world countries where donor corneas are not culturally acceptable. Multiple models and devices are necessary to accommodate the various pathological states of the corneas.

Polymers and Corneal Implants

Many attempts have been made to create artificial corneas or keratoprostheses in order to replace donor cornea grafts. Such attempts have often failed because of an absence of healing and permanent attachment between the periphery of the synthetic device and the residual rim of the host cornea. As a result, tissue necrosis, leakage of aqueous humor, epithelial down-growth, and intraocular infection frequently occur occurred.

Numerous keratoprostheses have been developed using a variety of polymer materials such as poly-(2-hydroxy ethyl methacrylate) (pHEMA), poly-(methyl methacrylate), poly-vinyl alcohol, or poly-(ethyl vinyl alcohol), and in some instances mixed with collagen or hyaluronic acid, (Chirila, 2001; U.S. Pat. No. 5,458,819 (Chirila et al., issued Oct. 17, 1995); U.S. Pat. No. 5,300,116 (Chirila et al., issued Apr. 5, 1994); Hicks et al., 1998a; 1998b; Guisti et al., 1994, Legais et al., 1995; 2001; Legeais and Renard, 1998, Robert et al., 2001; Trinskaus-Randell et al., 1988; 1997; Trinskaus-Randell and Nugent, 1998; Vijayasekaran et al., 1998; 2000; Wu et al., 1998; U.S. Pat. No. 5,436,135 by Tayot et al; Jul. 25, 1995). Most keratoprostheses in development consist of a central transparent optical element, surrounded by a porous opaque material as a peripheral rim that allows penetration and proliferation of stromal keratocytes and the subsequent synthesis of collagen within the material. The peripheral rim has been made of different polymers such as polybutylene-polypropylene, and expanded poly(tetrafluoroethylene). U.S. Pat. No. 6,005,160 (Hsiue et al; Dec. 21, 1999) describes a heterofunctional membrane for application as an artificial cornea using polyacrylic acid or polymethacrylic acid, and then bonded with collagen, or HEMA, or with polyethylene oxide. A hetero, bi-functional biomedical surface can also be developed with 2-methacryloyloxyethyl phosphorylcholine, or 2-methacryloyloethyl phosphorylcholine. Such a product has good transparency, hydrophilicity and high biocompatibility. These devices have been more or less successful (e.g., remain in place for 6 months). However, the skirt of most of them have low tensile strength leading to suturability problems, inflammatory reaction, and subsequent extrusion of the keratoprosthesis. A keratoprosthesis made of a transparent pHEMA core is undergoing clinical trials (Chirila et al., 2001).

Other corneal implants have been designed to correct the cornea curvature by inserting an intrastromal implant using polymers in a form of microporous hydrogel material. However, extrusion is still a major issue, as it is undesirable because it tends to cause clinical complications and product failure. For example, a polymerized PEG (by gamma radiation) hydrogel has been designed to be injectable into the stroma (U.S. Pat. No. 6,102,946 by Nigam A, issued Aug. 15, 2000). U.S. Pat. No. 5,994,133 (Meijs et al; Nov. 30, 1999) reports a corneal implant made with macromonomer of per-fluoropolyether. U.S. Pat. No. 4,702,244 (Mazzocco; Oct. 27, 1987) reports a polyurethane/collagen hydrogel compound for an intraocular artificial lens. US patent application 20010018612 (Carson DR, published Aug. 30, 2001) describes an intraocular lens for long term implantation in the cornea composed of two hydrogel materials made of copolymer of N-vinyl-pyrrolidone and 2-phenylethyl methacrylate and the second polymer is based on glyceryl methacrylate.

Biological and Cell-Seeded Materials

Human amniotic membrane can be used as replacement for full-thickness corneal defects. Although, corneal architecture is normally restored at long term with a layering of the epithelium and endothelium, with pigmentation and vascularization present in the deep layers of the cornea, amniotic membranes are susceptible to infectious contamination and transmission. Type IV collagen from placenta has been proposed to replace amniotic membranes (U.S. Pat. No. 5,436,135 (Tayot et al; Jul. 25, 1995)). U.S. Pat. No. 5,114,627 (Civerchia; May 19, 1992) describes a collagen hydrogel for promoting epithelial cell growth.

Collagen film or hydrogels can be used as cornea dressing or contact lens (Miyata et al., 1992). Most collagen materials have been chemically crosslinked to increase their resistance to biodegradation.

Alternatively, attempts have been made to reconstruct corneas in vitro from cell lines. Individual human corneal epithelial layers have been successfully maintained in culture as a stratified epithelium (Kahn et al., 1993; Araki-Sasaki et al., 1995). Successful reconstructions of corneas comprising the 3 main layers have also been reported using animal cells (Minami et al., 1993; Zieske et al., 1994), and more recently, a whole human cornea equivalent was reconstituted with biological polymers and cells that mimics the physiology of the human cornea and surrounding tissue (Griffith et al., 1999; Griffith et al., published international application PCT/CA99/00057 [published Jul. 29, 1999 as WO 99/37752]). PCT/CA99/00057 relates to reconstruction of in vitro cell-based models for use as animal alternatives in irritancy, toxicity, and drug efficacy testing.

There thus remains a great need for improved materials and systems for use in corneal implants, repair and transplantation.

SUMMARY OF THE INVENTION

The invention relates to an improved corneal implant or membrane therefor.

Accordingly, in a first aspect, the invention provides a corneal implant comprising a membrane, the membrane comprising a biological polymer and a polyacrylamide.

In an embodiment, the polyacrylamide is a poly(N-alkylacrylamide), such as poly(N-isopropylacrylamide).

In an embodiment, the biological polymer is selected from the group consisting of collagen, fibrin-fibrinogen, gelatin, glycoproteins, peptides, glycosaminoglycans, elastin and mixtures thereof. In embodiments, the peptide is selected from the group consisting of adhesive peptides, growth factors, cytokines and chemokines. The collagen may be selected from the group consisting of telocollagen and atelocollagen, including type I collagen. The collagen may be selected from recombinant collagen and collagen from a natural source. The collagen may be from an animal, e.g. a mammal, such as human, rat (e.g. from rat tail tendon), cow or pig.

In an embodiment, the biological polymer and polyacrylamide are present in a ratio of about 0.2:1.0 (w/w) to about 1.0:0.2 (w/w), in a further embodiment in a ratio of about 0.3:1.0 (w/w) biological polymer:polyacrylamide.

The membrane may further comprises chemical crosslinks, e.g. obtained by crosslinking with a carbodiimide crosslinking agent such as 1-(3-dimethylaminopropyl)-3-ethyl carbodiimide (EDC), or with the combination of a carbodiimide such as EDC and N-hydroxysuccinimide (NHS), for example using a previously reported method (Olde Damink et al., 1996).

In an embodiment, the cross-linked membrane comprises a characteristic selected from the group consisting of an elastic modulus less than about 10 MPa, a tensile strength at break of less than about 6 MPa, an elongation at break of less than about 20% and a tensile energy to break of less than about 0.5 mJ. In an embodiment, the membrane has a thickness of about 20 μm to about 400 μm, in a further embodiment about 50 μm to about 100 μm.

In an embodiment, the membrane comprises a characteristic selected from the group consisting of an elastic modulus less than about 10 MPa, a tensile strength at break of less than about 6 MPa, an elongation at break of less than about 80% and a tensile energy to break of less than about 2 mJ.

In embodiments, the implant may comprise a plurality of the above-mentioned membranes. In a further embodiment, the plurality of the above-mentioned membranes collectively comprise a characteristic selected from the group consisting of an elastic modulus less than about 10 MPa, a tensile strength at break of less than about 3 MPa, an elongation at break of less than about 60% and a tensile energy to break of less than about 2 mJ.

The invention further relates to a use of the implant for corneal repair or transplantation.

The invention further relates to a method for treating a corneal injury or defect of a subject, comprising applying to a cornea of a subject the above-mentioned implant. Such a subject may be a mammal, such as a human.

The invention also relates to a commercial package comprising the above-mentioned implant, together with instructions for its use as a corneal implant.

The invention further relates to a method for preparing the above-mentioned corneal implant, the method comprising: (a) providing a polymer mixture solution comprising a biological polymer and a polyacrylamide (e.g. a solution obtained by combining a biological polymer and a polyacrylamide); (b) transferring the solution onto a drying surface; (c) allowing the solution to dry to obtain a membrane for use in the corneal implant. In an embodiment, the biological polymer is collagen.

The method may utilize collagen provided as a solution in 0.02N acetic acid in water, having a collagen concentration of about 1.0-6.0 mg/ml, in a further embodiment 3.0-3.5 mg/ml. The method may utilize a poly(N-isopropylacrylamide) which may be provided as a solution of about 2-10% in water, in a further embodiment 4% in water. These solutions may be combined in a 1:1 ratio.

The drying surface may be a plastic dish (e.g. a non-treated culture dish) or a mold (e.g. a lens or cornea mold). In an embodiment, the method further comprises a crosslinking step using crosslinking agents such as EDC and/or NHS.

In the case where the implant comprises a plurality of membranes, the method further comprises layering together a plurality of the membranes so obtained. In an embodiment, the method further comprises crosslinking the membranes to each other, using for example the agents and methods described herein.

The invention further relates to a use of a membrane comprising a biological polymer and a polyacrylamide as a corneal implant.

The invention further relates to a use of a plurality of membranes as a corneal implant, wherein at least one of said membranes comprises a biological polymer and a polyacrylamide. In an embodiment, the plurality of membranes comprises inter-membrane chemical crosslinks. In an embodiment, the crosslinks are obtained by crosslinking with a crosslinking agent selected from the group consisting of (a) a carbodiimide crosslinking agent; (b) an N-hydroxysuccinimide; and (c) both (a) and (b). In an embodiment, the carbodiimide crosslinking agent is 1-(3-dimethylaminopropyl)-3-ethyl carbodiimide.

The invention further relates to a commercial package comprising a membrane, the membrane comprising a biological polymer and a polyacrylamide, together with instructions for its use as a corneal implant.

The invention further provides a method for treating a condition characterized by a corneal defect, comprising applying the implant of the invention to a cornea of a subject. In an embodiment, the subject is a mammal, in a further embodiment, a human.

The invention also provides a commercial package comprising the implant of the invention together with instructions for treating a condition characterized by a corneal defect.

DETAILED DESCRIPTION OF THE INVENTION

Figure 1A:
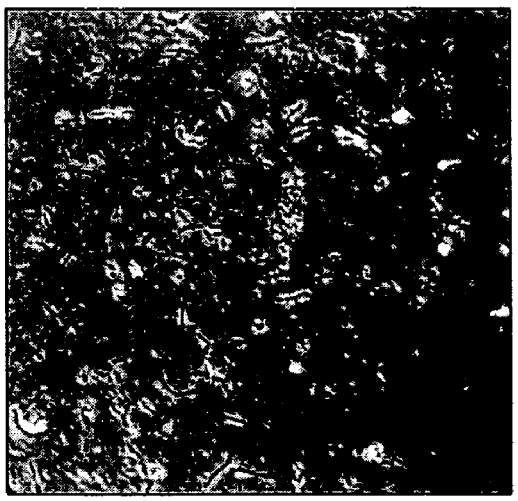
FIG. 1: Morphological aspect of the collagen-pNIPAAm specimens. In A, the collagen-PNIPAAm exhibits some collagen fibrils in solution prior to the drying process. The wet mixture appeared similar to the mixture obtained following the drying process. In B, histological sections of pNIPAAm-collagen membranes are presented. If a 10-20% size reduction due to the formaldehyde fixation is considered, membrane thickness is about 300-400 μm. Collagen fibrils can be seen relatively oriented in the plane of the membrane. In C, pNIPAAm has been mixed with fibrin polymer, the resulting gel consisting of a network of filamentous structures. Bar=100 μm.

The invention is in the field of opthalmology. In embodiments, the invention relates to a membrane which serves as the basis of a substitute for corneal implant or graft (i.e., penetrating keratoplasty), keratoprosthesis and to a replacement of amniotic membrane used as corneal implant and support for cultured epithelial and precursor cells. In embodiments, the substitute, i.e. the membrane or corneal implant of the invention, can be transplanted onto the cornea to assist cornea wound healing after eye surgery, cornea injury and disorders, or excimer laser surgery.

In an aspect, the invention relates to a corneal implant or keratoprosthesis comprising a membrane of the invention, which is produced by the combination of biological polymer, such as collagen, and a polyacrylamide, e.g. a polyalkylacrylamide such as poly(N-isopropylacrylamide) (pNIPAAm). The use of such synthetic polymers is advantageous as it provides good transparency and strength to the membrane, contributing to its use as a corneal implant. Prior to the studies described herein, pNIPAAm and its derivatives have not been used in any cornea or ocular device. In an embodiment, the biological polymer is collagen, in a further embodiment, type I telocollagen, a soluble form of non-pepsinized collagen that may for example be purified from rat tail tendon (RTT). Other sources of collagen, including mammalian sources, such as bovine, porcine, and human telocollagen or atelocollagen (pepsin or pronase digested telocollagen) may also be used. Collagen may also be from a recombinant source. In the examples described below, the synthetic polymer pNIPAAm homopolymer has been used.

"Corneal implant" as used herein refers to any material or device which may be applied to or comes in contact with the cornea of a subject. In an embodiment the subject is a mammal, in a further embodiment, a human. Such an implant may be used for repair or replacement of a cornea or a portion thereof, or as a cornea wound dressing, due to defects for example caused by corneal injury or disease. In a preferred embodiment, the implant is substantially transparent.

pNIPAAm-Based Materials

The pNIPAAm family of polymers is one of the few synthetic materials which support cell in-growth and growth of polymer encapsulated cells (Vernon et al 1999; Stille et al 1999). pNIPAAm has been extensively studied in vitro for cell culture use that demonstrates its non cytotoxicity (Takezawa et al 1990). Takezawa et al. (1992) have combined collagen with pNIPAAm as cell culture substrate in order to form spheroids, producing only a thin (2 μm) layer of collagen-pNIPAAm. Moreover, U.S. Pat. No. 6,030,634 (Wu et al.; Feb. 29, 2000) describes the combination of pNIPAAm with gelatin (denaturated collagen) which results in a polymer gel having the properties of an interpenetrating polymer network structure with a shrinking temperature of 35° C., having surgical application for the repair of damaged tissue, but not replacement or substitution. Further, corneal applications are not contemplated nor mentioned. An improved shrinking rate for a drug delivery system using such network structure is also described. Furthermore, activated pNIPAAm has also been conjugated to protein A, various enzymes, biotin, phospholipids, RGD peptide sequences, and other interactive molecules such as monoclonal antibodies (as described in U.S. Pat. No. 4,780,409; Oct. 25, 1988; Monji and Hoffman, 1987).

The polymer gel compositions of the present invention comprises a matrix, such as an interpenetrating pNIPAAM-collagen hydrogel network which leads to strengthen the final collagen-based product while keeping its transparency. In embodiments, the membrane of the invention may be made with different ratios of collagen to pNIPAAm. In an embodiment, the collagen to pNIPAAm ratio is in the range of about 0.2:1.0 to 1.0:0.2 (w/w). In an embodiment, the collagen to pNIPAAm ratio is about 0.3:1.0 w/w, which is the preferred ratio for corneal implant design.

Collagen can be replaced or mixed with other biological polymers, including proteins such as gelatin, fibrin-fibrinogen, glycosaminoglycans, elastin, and glycoproteins or peptides such as adhesive peptide sequences, cytokines, chemokines or growth factors.

The membranes can be layered together, in a further embodiment laminated together, to form a composite material in which thickness can be a controlled parameter. In addition, a multilayered membrane may result in the guidance of the stroma regeneration within the implant. As such, in an embodiment, a corneal implant of the invention may comprise a plurality of the membranes of the invention. The layered membranes in such a structure may be heterogeneous, i.e. having different polymeric compositions and ratios of components. In addition, a mixture of crosslinked and non-crosslinked membranes may be used. The membranes in such a layered structure may be crosslinked to one another using for example the crosslinking agents and methods described herein.

A variety of agents or compounds (crosslinking, plasticizer, etc.) can be introduced during manufacturing of the membrane before and/or after the formation of the membrane. Depending on the step in which the agent or compound is added, the physicochemical and biological properties of the membrane may vary. In embodiments, the membrane of the invention may be crosslinked with different agents. In an embodiment, EDC and NHS are the crosslinking agents.

pNIPAAm can be modified physically to provide different biophysical and biological properties for different ophthalmic applications (e.g., wound dressings) and mixed with collagen. In a further embodiment, collagen membranes can be crosslinked chemically either during the procedure or afterwards.

In an embodiment, the membrane is transparent and its thickness range is between about 20 μm and about 400 μm, depending upon hydration. In a further embodiment, the thickness of the membrane is in the range of about 50 μm to about 100 μm. Different thicknesses can be produced, as well as different front and back curvature for cornea replacement.

In an embodiment, the membrane comprises an elastic modulus of less than about 10 MPa, a tensile strength at break of less than 6 MPa, an elongation at break of less than 80% and a tensile energy to break of less than 2 mJ.

In an embodiment, the membrane of the invention is strong enough to support suturing stresses. Its physical properties such as strength and elasticity can be modified by crosslinking (e.g. with carbodiimide-type crosslinking agents such as EDC), but other crosslinking agents (e.g., NHS) and plasticizers such as glycerol can be used. The physical properties of the membrane may be modified for example as a function of rehydration, or via the presence of lipids and/or proteins. Physical modification of pNIPAAm can lead to different properties that may enhance biological and biophysical characteristics for corneal implants or membrane substitutes.

The membrane of the invention provides a device which remains robust and optically clear in the eye for extended periods of time.

In the embodiments of the invention, there is cell ingrowth into the polymeric membrane, and epithelialization over the membrane with no hyperplasia. The membrane may induce the deposition of organized extracellular matrix proteins resembling the cornea stroma with close reorganisation of the newly deposited collagen and stromal cells.

The membrane of the invention may further comprise/have associated with it various compounds e.g. drugs, biological materials (e.g. peptides/proteins, lipids, etc.), crosslinkers, plasticizers, cytokines, etc. to fulfill or further contribute to an aspect of the desired functionality of the corneal implant in any particular situation. Such agents or compounds may be introduced during the making of the membranes or after their formation.

The invention further relates to a method of preparing a corneal implant of the invention, comprising combining a biological polymer and a polyacrylamide (or providing such a mixture), and allowing the mixture to dry to form a membrane for use as a corneal implant. In embodiments, the biological polymer is collagen provided as a collagen solution of about 1-6 mg/ml, in a further embodiment, about 3.0-3.5 mg/ml (e.g. in 0.2N acetic acid in water), and the polyacrylamide is pNIPAAm provided in a solution of about 2-10%, in a further embodiment, about 4% in water. In an embodiment, the solution of the biological polymer and the polyacrylamide may be combined in a ratio of about 1:1. The polymer mixture may be poured into a suitable dish (e.g. a plastic culture [e.g. non-treated] dish) or mold (e.g. a lens or cornea mold) for drying. Drying may be allowed to proceed until for example a constant weight (e.g. about 1-10% water residue, in a further embodiment about 7% water residue) is reached. Drying may be performed under sterile conditions, under a laminar flow hood. Drying may be performed at room temperature (15-22° C.), for example for a period of about 2-4 days. The preparation may further involve a crosslinking step, using for example a crosslinking agent such as EDC and/or NHS. The resulting membrane is typically rehydrated with a suitable solution prior to its use for cornea implantation.

The invention further relates to the use of a membrane of the invention as a corneal implant, e.g. for application to the cornea for repair or replacement of damaged or otherwise inadequate cornea, thus for the treatment of a corneal defect, disorder, injury or disease.

The invention further relates to a method of treating a condition characterized by a corneal defect (e.g. corneal disorder, injury or disease), said method comprising administering to a subject in need thereof a corneal implant of the invention.

The invention further relates to a commercial package comprising a membrane of the invention together with instructions for its use as a corneal implant, e.g. for application to the cornea for repair or replacement of damaged or otherwise inadequate cornea, thus for the treatment of a corneal defect, disorder, injury or disease.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. In the claims, the word "comprising" is used as an open-ended term, substantially equivalent to the phrase "including, but not limited to". The following examples are illustrative of various aspects of the invention, and do not limit the broad aspects of the invention as disclosed herein.

Throughout this application, various references are referred to describe more fully the state of the art to which this invention pertains. The disclosures of these references are hereby incorporated by reference into the present disclosure.

EXAMPLES

Example 1

Collagen-pNIPAAm Membranes

A sterile RTT collagen solution of 3.0-3.5 mg/ml (w/v) in acetic acid (0.02N in water) is made, and kept at 4° C. A 4% (w/v) solution of pNIPAAm homopolymer is made in water (ddH2O) and sterilized by autoclaving or by filtering (0.24tm). The 4% solution of pNIPAAm is diluted to a 1% solution with sterile ddH2O. The 0.30-0.35% solution of collagen and the 1% solution of pNIPAAm are mixed (1:1 vol/vol) in a sterile test tube at 4° C. by pumping with a pipette until well dispersed. Cold mixing will avoid any premature gelification or fibrillogenesis of the collagen during this procedure. Collagen-pNIPAAm is then poured into a plastic dish (non-treated culture dish) or a mold (e.g., lens or cornea mold) and left air-drying under sterile conditions in a laminar flow hood for at least 2-3 days at room temperature. After drying to constant weight (~7% water residue) at room temperature, under laminar flow at relatively constant humidity, the formed membrane is removed from the mold after soaking for a short period (hours) in a sterile buffered solution (e.g., Hank's balanced salt solution or HBSS) at room temperature. The sterile membrane is ready to be used for cornea implantation or for a transplantable membrane support for epithelial cells.

Conversely, RTT collagen solution that is not mixed with pNIPAAm as reported above, and only diluted in water or buffer at 1:1 ratio, fails to become a transplantable and suturable collagen membranes after drying.

Example 2

Fibrin-pNIPAAm Membranes

A sterile fibrinogen (fraction I; type I-S from bovine plasma) solution (3 mg/ml in HBSS) is mixed with a 1% pNIPAAm solution as reported in Example 1. During mixing, thrombin (50 U/ml purchased from Parke Davis) is added at a final concentration of 0.03:1 v/v (thrombin:fibrin), and incubated for 10-15 min at 37° C. to allow gelification (hydrogel) in a culture well. This procedure strengthens the fibrin gel, probably by aiding the development of a filamentous network as shown on FIG. 1C.

Example 3

Crosslinked Membranes

A sterile RTT collagen viscous solution and a 1% (w/v) solution of pNIPAAm are made as described in Example 1. The 0.30-0.35% solution of collagen and the 1% solution of pNIPAAm are mixed (1:1 vol/vol) with a 10% stock solution of 1-(3-dimethylaminopropyl)-3-ethyl carbodiimide hydrochloride (EDC) in water to give a final EDC concentration of 0.5; 0.1; or 0.05% (w/v) in a sterile test tube at 40° C. by pumping with a pipette until well dispersed. The collagen-pNIPAAm-EDC mixture is then poured into a plastic dish (non-treated culture dish) or a mold (e.g., lens or cornea molds) and left air-drying under sterile conditions in a laminar flow hood for at least 2-3 days at room temperature. After drying to constant weight (~7% water residue), an interpenetrating network of pNIPAAm in cross-linked collagen is formed. Each membrane is removed from the mold after soaking in a sterile buffered solution (e.g., HBSS) at room temperature. Among the three different concentrations of EDC tested, the one with the lowest concentration gave the most reliable procedure to toughen the membrane. The sterile membranes can be soaked in HBSS containing glycine (5% in HBSS) to remove residual unreactive crosslinking agent. Membranes are further rinsed in HBBS (at least 3 times). Thus, they are ready to be used for cornea implantation or for a transplantable membrane support for epithelial cells.

Example 4

Alternative Thick Membranes

Membranes from Examples 1 and 3 are used to form a thicker membrane that are produced by sticking one or several membranes together. For this procedure, hydrated membranes are bound to each other using a solution of 0.5% EDC solution. The resulting membranes of various thicknesses are left to dry, then rinsed as described in Example 1.

As an Example of Procedure:

after rehydration of the membrane, excess water is removed one rehydrated membrane is left bonded to the bottom of the dish or mold the other membrane to be glued to the first one is released from its dish or mold the EDC solution (10 μl of 10% stock EDC solution per cm$^2$ of membrane) is poured over the unreleased membrane. EDC plays the role of a glue between the 2 membranes.

at once, the second membrane (released one) is laid down onto the solution and stuck to the unreleased membrane, combined membranes are dried, later rehydrated, and finally rinsed as described in Example 1.

Different combinations can be made such as one crosslinked membrane sandwiched between two uncrosslinked membranes, or other alternatives.

Example 5

Incorporation of Compounds

A variety of agents or compounds (e.g., crosslinking, plasticizer, drugs, cytokines) can be introduced during the making of the membranes from examples I to IV. Compounds can be introduced either during the mixing of both collagen and pNIPAAm or after the formation of a membrane. The latter can be dried, thereby, the agents can be introduced during the rehydration process. Otherwise, the agents can be introduced on the rehydrated membrane. The physicochemical and biological properties may vary (Table I).

Example 6

Physical Properties

Figure 1B:
Figure 1C:
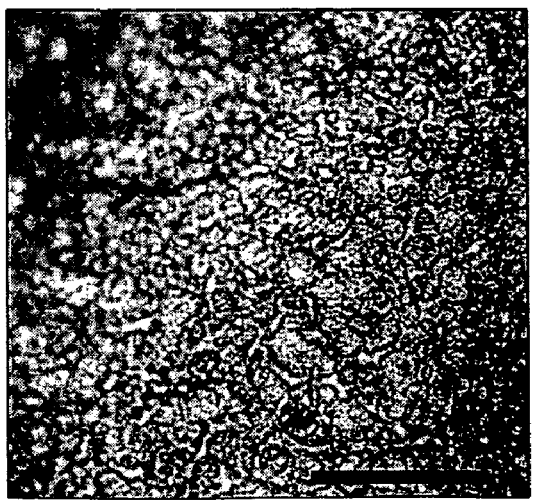

The rehydrated implants from examples 1 and 3 to 5 are strong enough to support surgical manipulation, suture thread and needle (Table I). They are relatively flexible. The presence of proteins and lipids (e.g., Albumax®) is likely to strengthen the membranes. Similar properties are also observed in the presence of glycerol combined at the time of mixing collagen and PNIPPAAm solutions. The membrane thickness can vary from 20 to 400 μm after hydration (FIG. 1).

TABLE I: Shearing characteristics of the resulting membranes produced in different experimental conditions. Shearing forces are roughly determined by handling the specimen between 2 forceps in opposite directions. The membranes result from the mixture of collagen and PNIPAAm. Collagen can be prepared by making a solution either in acetic acid at pH 4.0 (Coll(ac.ac.)) or in water at pH 3.0 with HCl(Coll(HCl)). A crosslinking agent such as EDC is introduced either during the mixture or after the formation of a membrane. The latter fragilizes the membrane. Glycerol can be used as a plasticizer. Albumax (a lipid rich bovine serum albumin, purchased from GIBCO/BRL) can be added during rehydration with Hank's balanced salt solution (HBSS). Other components can be introduced at different periods to induce different properties.

| Collagen (Coll) | Additional components added to the collagen-PNIPAAm mixture | Components added during rehydration (HBSS+) | Results (N = 1– 2) |
|---|---|---|---|
| Coll (ac. ac.) | | | strong |
| Coll (HCl) | | | strong |
| Coll (HCl) | 0.05% EDC | | very strong |
| | 0.1% EDC | | strong |
| | 0.5% EDC | | more fragile |
| Coll (HCl) | | 0.1% EDC | fragile |
| | | 0.5% EDC | fragile |
| Coll (ac. ac.) | 0.5% Glycerol | | strong |
| | 1% Glycerol | | strong |
| Coll (ac. ac.) | | Albumax (2X) | very strong |

Example 7

Biomechanical Properties

Composite collagen-PNIPAAm membranes from Example 1 were uncrosslinked (1M) or crosslinked by a carbodiimide derivative, the 1-(3-dimethylaminopropyl)-3-ethyl carbodiimide (1Mes); other membranes were layered by chemically binding 2 sheets of the collagen-PNIPAAm composite which were uncrosslinked (2M) or crosslinked (2Mes). Chemical binding was performed with the same carbodiimide.

Biomechanical tests were performed on membranes using an Instron Apparatus (Canton, Mass., USA). Strips of membranes were placed between the two grips of the apparatus and uniaxial tension was applied. Elongation of the membranes were recorded and analyzed (Table II).

Table II. Biomechanical assessments of uncrosslinked and crosslinked membranes. Means and standard errors of means are presented. These results were from 2 separate experiments of 3 samples each.

|  | Elastic Modulus MPa | Tensile Strength at break MPa | Extensibility at break % elongation at break | Tensile Energy to break mJ |
|---|---|---|---|---|
| 1M | 0.26 ± 0.06 | 0.12 ± 0.03 | 67.1 ± 14.7 | 0.17 ± 0.03 |
| 1Mes | 1.9 ± 0.78 | 3.27 ± 1.72 | 8.34 ± 4.8 | 0.19 ± 0.07 |
| 2M | 2.73 ± 0.41 | 0.73 ± 0.11 | 50.1 ± 4.03 | 1.01 ± 0.16 |
| 2Mes | 6.26 ± 3.03 | 1.41 ± 0.64 | 8.05 ± 2.63 | 0.08 ± 0.02 |

Carbodiimide crosslinking of collagen-PNIPAAm improved the strength of the membranes, particularly with the one-layer membrane, which exhibited an associated increased elasticity and toughness. The two-layered membranes were very elastic, probably due to a sliding effect within the 2 membranes. Although the strength of the two-layered membranes was weaker than the one-layer membrane, the overall toughness was sustained. The biomechanical properties of the membranes are similar to those reported for the human cornea (Zheng et al., 2001; Wang et al., 2001).

Example 8

In Vitro Cell Growth

Human stromal cells or keratocytes were seeded at $5 \times 10^5$ cells per $cm^2$ onto the collagen-pNIPAAm membranes from Example 1. They were then grown in the presence of culture medium and serum for 7 days. Stromal cells form a cell layer on the surface of the membrane as seen on histological section (see FIG. 1).

Figure 2:
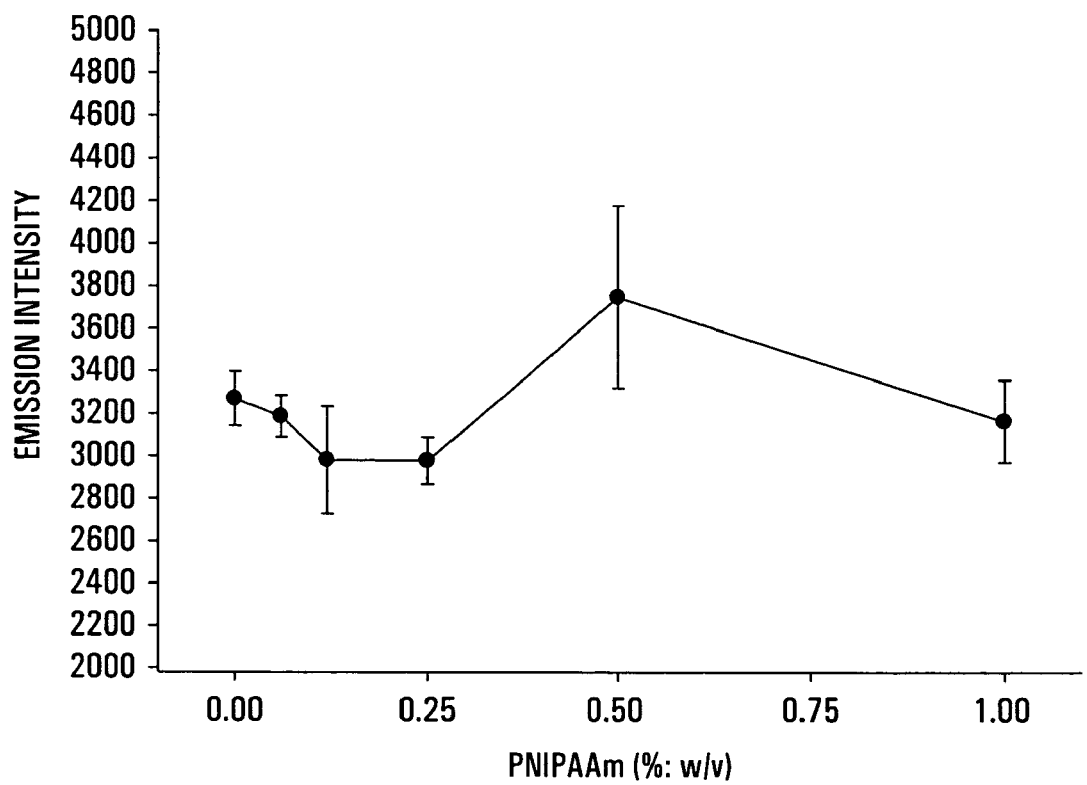
FIG. 2: Quantification of the growth of endothelial cells seeded in plastic dish in the presence of 10% fetal calf serum and endothelial cell growth supplement for 4 days. During this period, solutions of pNIPAAm were added at different dilutions in culture medium. Cell growth was not impaired by the presence of the polymer in cultures. Statistic analysis did not show any significant difference between these concentration conditions.

In other experiments, pNIPAAm was dissolved in the culture medium. Human endothelial cells were grown in the presence of the polymer for 5 days at different concentrations (0; 0.06; 0.12; 0.25 and 1.0 mg/ml). Endothelial cell numbers were determined by spectrofluorometry after staining cells with a DNA-specific dye (Hoechst 33342). Cell growth was not impaired by increasing concentration of pNIPAAm (no significant difference by ANOVA test) (see FIG. 2).

Example 9

In Vivo Biocompatibility

Figure 3B:
FIG. 3: Cornea observation after collagen-pNIPAAm membrane implantation in a cornea defect in rabbit eye. At day one, the membrane is in place well secured and transparent (A). The fluorescence shows the wound site (B). By day six, the defect is still clear (C) and fluorescence staining is minimal (D) that correspond to the presence of a reepithelialisation of the implant.
Figure 3D:
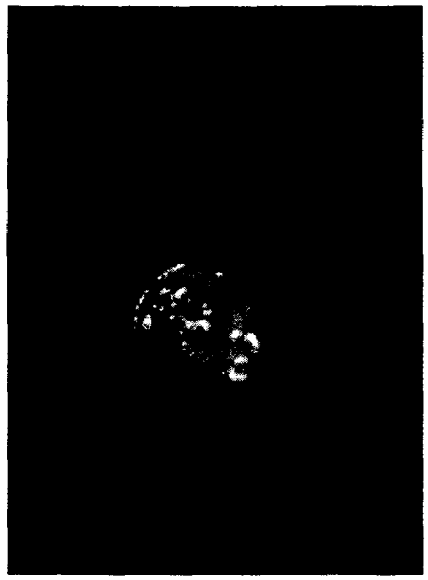
Figure 3A:
Figure 3C:
Figure 4A:
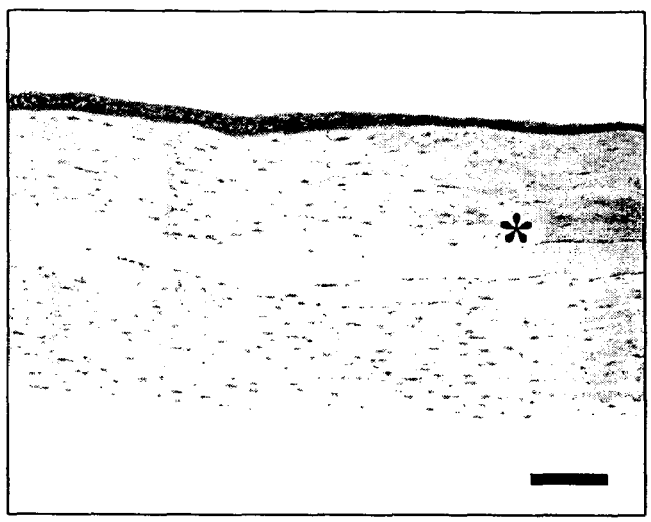
FIG. 4: Histological section of the collagen-pNIPAAm (A) and amniotic membrane (B) implant in rabbit cornea after 12 days of implantation. The collagen-pNIPAAm implant (arrows) is present within the stromal regeneration and the implant is uniformly covered with host epithelial cells. The stromal reaction is well oriented as in normal stroma with stromal cells between collagen fibers. No inflammatory or immune cells can be seen in the nearby of the implant. In B, the amniotic membrane is likely to be biodegraded and a epithelial hyperplasia can be observed in the periphery of the cornea defect. In C, the microsopic image of the collagen-pNIPAAm implant shows that the polymeric membrane (pm) is completely innervated 3 months after surgery. Nerves (arrowheads) are observed extending into the polymer. Bar=250 μm.
Figure 4B:
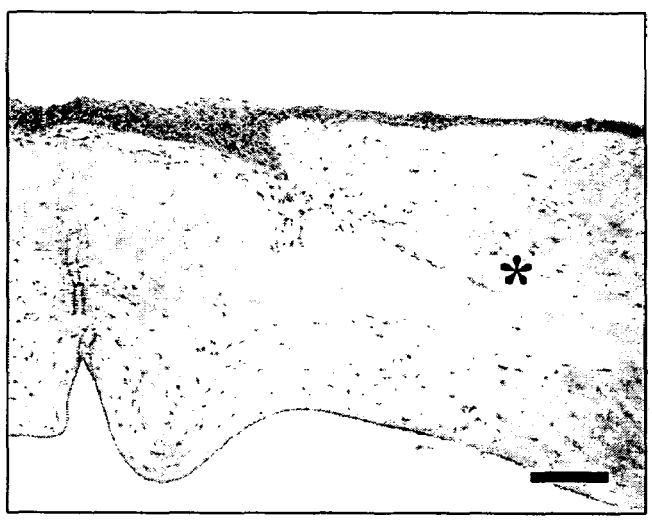
Figure 4C:
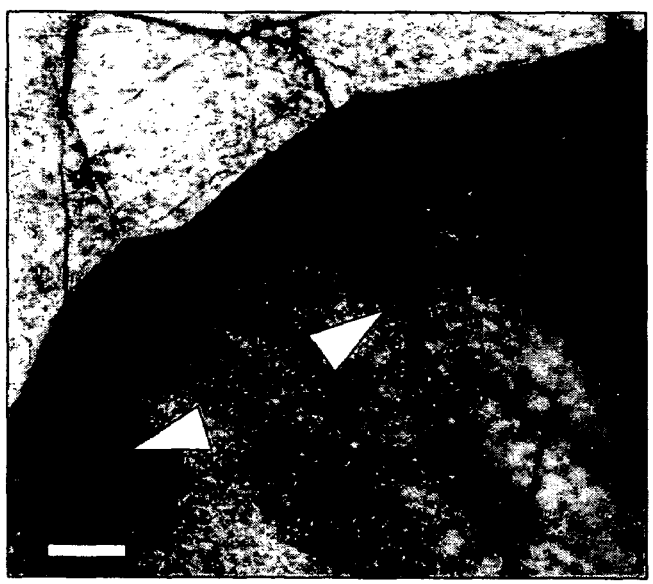

Collagen-pNIPAAm membranes from Example 1 were implanted into the corneas of 15 rabbits. Controls included sham operations and use of human amniotic membrane. FIGS. 3A&B show rabbit corneas at 3 days after surgery and fluorescein staining of the wound, respectively. By 3 days post-operative, re-epithelialization had occurred and fluorescein staining was minimal with the collagen implants. Conversely, 3 out of 9 rabbits with amniotic implants did not epithelialize by 3 days (FIGS. 3C&D). After 6 days a complete epithelialization was observed by direct observation and there was no fluorescein staining. This was comparable to observations made on corneas covered with amniotic membranes, which are now being used clinically to treat corneal epithelial damage due to disease or injury. Biopsies were taken at 12 days and show a complete epithelialization of the surface of the collagen-pNIPAAm membrane that was in place and non degraded (FIG. 4A). Around the implant the formation of an oriented stroma was observed, that is organized like the nearby stroma of the cornea. There was an absence of immune and inflammatory reaction. Furthermore, histological section of the cornea with the amniotic membrane showed a partial degradation of the membrane and a hyperplasia of the epithelial cell layer at the nearby of the cornea pocket (FIG. 4B). In addition, regenerating nerve axons were observed at the edges of the polymeric membrane underlying the wound at 11 days post-surgery and nerves had penetrated the periphery of the polymers by 28 days. By 3 months post-surgery, there was nerve re-growth into the polymeric membrane (FIG. 4C). Moreover, fine neurites are observed within the polymer-epithelial interface. Nerve regrowth into the membrane and overlying epithelium are consistent with previous observations of cornea nerve regeneration in rabbits (Tervo et al., 1994) and demonstrate the feasibility of transplantable artificial corneas that promote nerve in-growth following surgery. These artificial corneas could address the world donor cornea shortage problem while circumventing the problems resulting from the lack of nerve regeneration found in artificial keratoprosthesis.

REFERENCES

Araki-Sasaki K, Ohashi Y, Sasabe T. Hayashi K, Watanabe H, Tano Y, Handa H. (1995) An SV40-immortalized human corneal epithelial cell line and its characterization. Invest Opthalmol Vis Sci. 36(3):614-21.

Carson D R, US patent application 20010018612. Intracorneal lens. Aug. 30, 2001.

Chirila T V, (2001) An overview of the development of artificial corneas with porous skirts and the use of PHEMA for such an application. Biomaterials 22:3311-3317.

Chirila T, Constable I, Crawford G J, Russo A V. (U.S. Pat. No. 5,458,819) Method of producing keratoprosthesis. Oct. 17, 1995.

Chirila et al. (U.S. Pat. No. 5,300,116) Keratoprosthesis. Apr. 5, 1994.

Civerchia L. (U.S. Pat. No. 5,114,627) Method for producing a collagen hydrogel. May 19, 1992.

Giusti P, Lazzeri L, De Petris S, Palla M, Cascone M G. (1994) Collagen-based new bioartificial polymeric materials. Biomaterials. 15(15):1229-33.

Griffith M., Osborne R., Munger R., Xiong X., Doillon C. J., Laycock N. I. C., Hakim M., Song Y., Watsky M. A., Functional human corneal equivalents constructed from cell lines. Science 286: 2169-2172, 1999.

Griffith M., Watsky M., Doillon C. J., Song Y. Artificial cornea. Published international application PCT/CA99/00057, published Jul. 29, 1999 as WO 99/37752.

Hicks C R, Vijayasekaran S, Chirila T V, Platten S T, Crawford G J, Constable I J. (1998a) Implantation of PHEMA keratoprostheses after alkali burns in rabbit eyes. Cornea. 17(3):301-8.

Hicks C R, Chirila T V, Clayton A B, Fitton J H, Vijayasekaran S, Dalton P D, Lou X, Platten S, Ziegelaar B, Hong Y, Crawford G J, Constable I J. (1998b) Clinical results of implantation of the Chirila keratoprosthesis in rabbits. Br J Opthalmol 82(1): 18-25.

Hsiue G H, Lee S D, Chung PCT. (U.S. Pat. No. 6,005,160). Heterobifunctional membrane in application of artificial cornea. Dec. 21, 1999.

Kahn C R, Young E, Lee I H, Rhim J S. (1993) Human corneal epithelial primary cultures and cell lines with extended life span: in vitro model for ocular studies. Invest Opthalmol Vis Sci. 34(12):3429-41.

Legeais J M, Renard G, Parel J M, Savoldelli M, Pouliquen Y. Keratoprosthesis with biocolonizable microporous fluorocarbon haptic. (1995) Preliminary results in a 24-patient study. Arch Opthalmol. 13(6):757-63.

Legeais J M, Parc C, d'Hermies F, Pouliquen Y, Renard G. (2001) Nineteen years of penetrating keratoplasty in the Hotel-Dieu Hospital in Paris. Cornea. 20(6):603-6.

Legeais J M, Renard G. (1998) A second generation of artificial cornea (Biokpro II). Biomaterials. 19(16):1517-22.

Mazzocco T, (U.S. Pat. No. 4,702,244) Surgical device for implantation of a deformable intraocular lens. Oct. 27, 1987.

Meijs G F, Laycock B G; Griffiths M C, Cheong E, Steele J G, Graham J., (U.S. Pat. No. 5,994,133) Cell growth substrate polymer. Nov. 30, 1999.

Minami Y, Sugihara H, Oono S. (1993) Reconstruction of cornea in three-dimensional collagen gel matrix culture. Invest Opthalmol V is Sci. 34(7):2316-24.

Miyata T, Taira T, Noishiki Y. (1992) Collagen engineering for biomaterial use. Clinical Mat. 9:139-148.

Monji N, Hoffman A S, Priest J H, Houghton R L., (U.S. Pat. No. 4,780,409) Thermally induced phase separation immunoassay. Oct. 25, 1988.

Monji N, Hoffman A S. (1987) A novel immunoassay system and bioseparation process based on thermal phase separating polymers. Appl Biochem Biotechnol. 14(2): 107-20.

Nigam A, (U.S. Pat. No. 6,102,946) Corneal implant and method of manufacture. Aug. 15, 2000.

Olde Damink L H, Dijkstra P J, van Luyn M J, van Wachem P B, Nieuwenhuis P, Feijen J. (1996) Cross-linking of dermal sheep collagen using a water-soluble carbodiimide. Biomaterials 17: 765-773.

Robert L, Legeais J M, Robert A M, Renard G. Corneal collagens. Pathol Biol (Paris). 2001 May; 49(4):353-63.

Stille R A, Burghardt W R, Healy K E. (1999) Synthesis and characterisation of injectable poly(N-isopropylacrylamide)-based hydrogels that support tissue formation in vitro. Macromolecules 32:7370-79.

Takezawa T, Mon Y, Yoshizato K. (1990) Cell culture on a thermo-responsive polymer surface. Biotechnology (NY).;8(9):854-6.

Takezawa T, Yamazaki M, Mon Y, Yonaha T, Yoshizato K. (1992) Morphological and immuno-cytochemical characterization of a hetero-spheroid composed of fibroblasts and hepatocytes. J Cell Sci. 101: 495-501.

Tayot J L, Tardy M., (U.S. Pat. No. 5,436,135) New preparation of placenta collagen, their extraction method and their applications. Jul. 25, 1995.

Tervo K., Latvala T M, Tervo T M T. (1994) Recovery of corneal innervation following photorefractive keratoablation. Arch. Opthalmol. 112:1466-1470.

Trinkaus-Randall V, Wu X Y, Tablante R, Tsuk A. (1997) Implantation of a synthetic cornea: design, development and biological response. Artif Organs. 21:1185-91.

Trinkaus-Randall V. Capecchi J, Newton A, Vadasz A, Leibowitz H, Franzblau C. (1988) Development of a biopolymeric keratoprosthetic material. Evaluation in vitro and in vivo. Invest Opthalmol V is Sci. 29:393-400.

Trinkaus-Randall V, Nugent M A. (1998) Biological response to a synthetic cornea. J Control Release. 53:205-14.

Vernon B, Kim S W, Bae Y H. (1999) Insulin release from islets of Langerhans entrapped in a poly(N-isopropylacrylamide-co-acrylic acid) polymer gel. J Biomater Sci Polym Ed. 10:183-98.

Vijayasekaran S, Fitton J H, Hicks C R, Chirila T V, Crawford G J, Constable I J. (1998) Cell viability and inflammatory response in hydrogel sponges implanted in the rabbit cornea. Biomaterials 19:2255-67.

Vijayasekaran S, Chirila T V, Robertson T A, Lou X, Fitton J H, Hicks C R, Constable I J. (2000) Calcification of poly (2-hydroxyethyl methacrylate) hydrogel sponges implanted in the rabbit cornea: a 3-month study. J Biomater Sci Polym Ed. 11:599-615.

Wang H, Prendiville P L, McDonnell P J, Chang W V. (1996) An ultrasonic technique for the measurement of the elastic moduli of human cornea. J Biomech. 29:1633-6.

Wu X Y, Tsuk A, Leibowitz H M, Trinkaus-Randall V. (1998) In vivo comparison of three different porous materials intended for use in a keratoprosthesis. Br J Opthalmol. 82:569-76.

Wu C, Juang S (U.S. Pat. No. 6,030,634) Polymer gel composition and uses therefor. Feb. 29, 2000.

Zeng Y, Yang J, Huang K, Lee Z, Lee X. (2001) A comparison of biomechanical properties between human and porcine cornea. J Biomech. 34:533-7.

Zieske J D, Mason V S, Wasson M E, Meunier S F, Nolte C J, Fukai N, Olsen B R, Parenteau N L. (1994) Basement membrane assembly and differentiation of cultured corneal cells: importance of culture environment and endothelial cell interaction. Exp Cell Res. 2 14:621-33.

What is claimed is:

1. A corneal implant for improving or correcting vision comprising a membrane saturated with a hydrating solution, said membrane consisting essentially of a dried solution of a mixture of a biological polymer and a polyacrylamide homopolymer.

2. The implant of claim 1, wherein the polyacrylamide homopolymer is a poly (N-alkylacrylamide).

3. The implant of claim 1, wherein the polyacrylamide homopolymer is poly (N-isopropylacrylamide).

4. The implant of claim 1, wherein the biological polymer is selected from the group consisting of collagen, fibrin-fibrinogen, gelatin, elastin and any combination thereof.

5. The implant of claim 4, wherein the collagen is selected from the group consisting of telocollagen and atelocollagen.

6. The implant of claim 4, wherein the collagen is a type I collagen.

7. The implant of claim 4, wherein the collagen is selected from the group consisting of recombinant collagen and collagen from a natural source.

8. The implant of claim 1, wherein the biological polymer and the polyacrylamide homopolymer are in a ratio of about 0.2:1.0 (w/w) to about 1.0:0.2 (w/w) biological polymer: polyacrylamide homopolymer.

9. The implant of claim 8, wherein the biological polymer and the polyacrylamide homopolymer are in a ratio of about 0.3:1.0 (w/w) biological polymer:polyacrylamide homopolymer.

10. The implant of claim 1, wherein the membrane has a thickness of about 20 μm to about 400 μm.

11. The implant of claim 10, wherein the membrane has a thickness of about 50 μm to about 100 μm.

12. A corneal implant for improving or correcting vision comprising a plurality of membranes, wherein at least one of said plurality of membranes is the membrane saturated with the hydrating solution as defined in claim 1.

13. A method of treating a condition characterized by a corneal defect, said method comprising applying the implant of claim 1 to a subject.

14. The method of claim 13, wherein said subject is a human.

15. The implant of claim 1, wherein the hydrating solution comprises a drug, a bioactive compound, a chemical crosslinking agent or a combination thereof.

16. The implant of claim 15, wherein the bioactive compound is selected from the group consisting of proteins, glycoproteins, adhesive peptides, glycosaminoglycans, lipids, cytokines, chemokines and any combination thereof.

17. The implant of claim 1, wherein the mixture is formed from a 0.30-0.35% solution of the biological polymer and a 2-10% solution of the polyacrylamide homopolymer.

18. A corneal implant for improving or correcting vision comprising a membrane saturated with a hydrating solution, said membrane consisting essentially of a dried solution of a mixture of biological polymer, a polyacrylamide homopolymer, and a chemical crosslinking agent.

19. The implant of claim 18, wherein the chemical crosslinking agent is selected from the group consisting of (a) a carbodiimide crosslinking agent; (b) a N-hydroxysuccinimide; and (c) both (a) and (b).

20. The implant of claim 19, wherein the carbodiimide crosslinking agent is 1-(3-dimethylaminopropyl)-3-ethyl carbodiimide.

21. A corneal implant for improving or correcting vision comprising a membrane saturated with a hydrating solution, said membrane consisting essentially of a dried solution of a mixture of a biological polymer, a polyacrylamide homopolymer, and a drug, a bioactive compound, or a combination of (i) a drug and a bioactive compound, (ii) a drug and a chemical crosslinking agent, (iii) a bioactive compound and a chemical cross-linking agent, or (iv) a drug, a bioactive compound and a chemical crosslinking agent.

22. The implant of claim 21, wherein the bioactive compound is selected from the group consisting of proteins, glycoproteins, adhesive peptides, glycosaminoglycans, lipids, cytokines, chemokines and any combination thereof.

* * * * *

UNITED STATES PATENT AND TRADEMARK OFFICE
CERTIFICATE OF CORRECTION

PATENT NO. : 7,476,398 B1 Page 1 of 1
APPLICATION NO. : 10/606796
DATED : January 13, 2009
INVENTOR(S) : Charles J. Doillon et al.

It is certified that error appears in the above-identified patent and that said Letters Patent is hereby corrected as shown below:

On the Title Page, Item (73) please add OTTAWA HEALTH RESEARCH INSTITUTE.

Signed and Sealed this

Thirty-first Day of August, 2010

David J. Kappos
*Director of the United States Patent and Trademark Office*